United States Patent [19]
Coates et al.

[11] Patent Number: 5,423,826
[45] Date of Patent: Jun. 13, 1995

[54] ANTERIOR CERVICAL PLATE HOLDER/DRILL GUIDE AND METHOD OF USE

[75] Inventors: Bradley J. Coates, Cordova, Tenn.; Gary L. Lowery, Gainesville, Fla.

[73] Assignee: Danek Medical, Inc., Memphis, Tenn.

[21] Appl. No.: 145,079

[22] Filed: Oct. 29, 1993

Related U.S. Application Data

[63] Continuation-in-part of Ser. No. 14,415, Feb. 5, 1993, Pat. No. 5,364,399.

[51] Int. Cl.[6] .............................................. A61B 17/58
[52] U.S. Cl. ........................................ 606/96; 606/69; 606/61
[58] Field of Search ...................... 606/53, 61, 69, 96, 606/104, 205

[56] References Cited

U.S. PATENT DOCUMENTS

| | | |
|---|---|---|
| 4,119,092 | 10/1978 | Gil .......................... 606/96 |
| 4,570,624 | 2/1986 | Wu . |
| 4,907,577 | 3/1990 | Wu . |
| 4,911,153 | 3/1990 | Border . |
| 5,057,111 | 10/1991 | Park . |
| 5,147,361 | 9/1992 | Ojima . |

OTHER PUBLICATIONS

Siebrandt MFGR Co. New Bone Instruments Brochure, Published Jul. 1, 1939, 3 pages.
Howard S. An, et al., "Surgical Exposure and Fusion Techniques of the Spine", *Spinal Instrumentation*, 1992, pp. 1-11.

*Primary Examiner*—Tamara L. Graysay
*Attorney, Agent, or Firm*—Woodard, Emhardt, Naughton Moriarty & McNett

[57] ABSTRACT

A drill and tap guide system is disclosed which can be mounted on a bone plate to provide a finn foundation for accurately drilling and tapping screw holes into vertebra to be instrumented. The drill and tap guide system includes an assembly support which is engaged to the plate by way of a positioning screw and cross pins mounting the positioning screw to the guide body. A tap sleeve and drill guide can then be supported by the assembly support, which both thereby provide accurate positioning for a drill. In another embodiment, the system includes a guide apparatus for holding a spinal plate and drilling and tapping the bone. The guide comprises two arms which pivot with respect to each other and a foot attached at the end of each arm. Each foot has a hook which is adapted to securely grasp a spinal plate and a pair of thru-holes. Each hole is aligned with a screw bore in a spinal plate when the guide assembly is engaged to the plate. The system further includes a number of double-headed fixation pins, which hold the plate in position against the cervical spine during drilling and tapping.

17 Claims, 15 Drawing Sheets

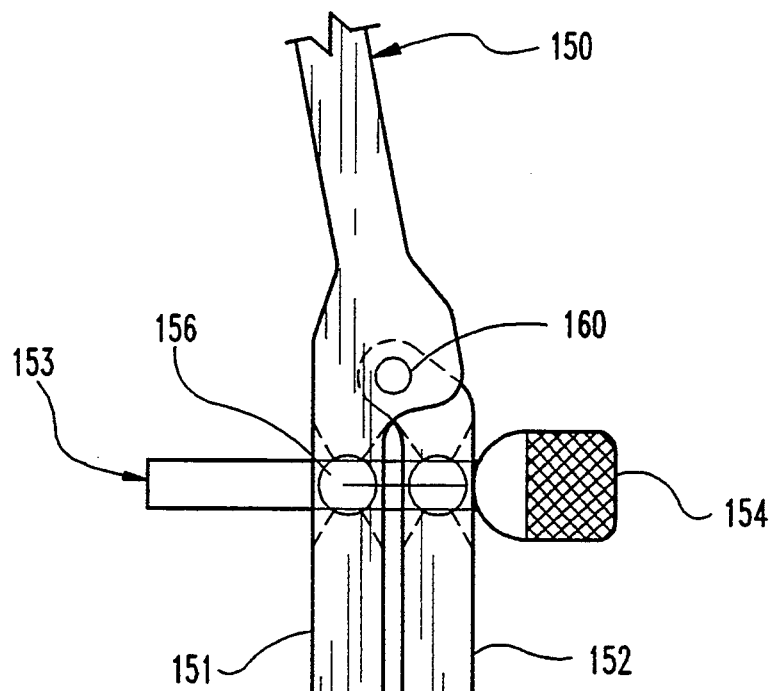
Fig. 14
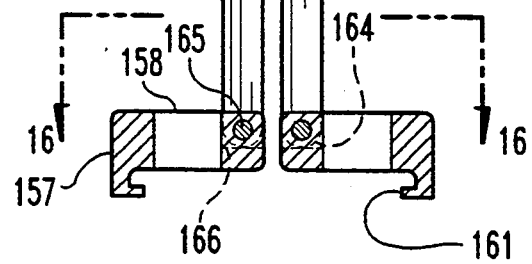

ANTERIOR CERVICAL PLATE HOLDER/DRILL GUIDE AND METHOD OF USE

This application is a continuation-in-part of application Ser. No. 08/014,415 filed on Feb. 5, 1993 now U.S. Pat. No. 5,364,399.

BACKGROUND OF THE INVENTION

The present invention concerns spinal instrumentation systems, such as for use with the cervical vertebrae. More particularly, the invention pertains to a plating system for use in treatment of the cervical spine.

Within the last decade, the use of fixation plates for treatment of spinal disorders or for fusion of vertebrae has grown considerably. While early procedures using fixation plates were at the lower lumbar levels, spinal fixation plates have recently found applications in the instrumentation of the cervical spine. Successful spinal instrumentation in this region is particularly difficult given the problems of safely accessing the instrumentation site.

The upper cervical spine can be approached either anteriorly or posteriorly, depending upon the spinal disorder to be treated. Many of the well known surgical exposure and fusion techniques of the cervical spine are described in the publication entitled *Spinal Instrumentation*, edited by Dr. Howard An and Dr. Jerome Cotler, particularly at pages 1-11. Of particular relevance to the present application are the exposure techniques and procedures for the anterior approach described at pages 1-5 of this publication, which disclosure is incorporated herein by reference. In this text, as well as in other documentation describing cervical spine surgical techniques, it is stressed that complications associated with the procedure can be devastating, such as injury to the brain stem, spinal cord or vertebral arteries. In addition, a lengthy procedure can lead to typical surgical complications.

On top of the normal complications associated with exposure and fusion of the cervical spine, implantation of a spinal fixation plate adds to the degree of risk and complication. In a cervical plating system of Synthes, Inc., it is necessary to locate the fixation plate over the vertebral levels to be instrumented and use this plate as a drill guide for drilling and tapping the bone in preparation for receiving a fixation screw. The system and procedure provide for a soft tissue protector in the manner of an elongated sleeve which is intended to minimize damage to the surrounding muscle and other tissues.

There is a need for a cervical plating system which minimizes the intrusion into the patient and reduces trauma to the surrounding soft tissue. Moreover, a system is required that allows for easy access to drill and tap the cervical vertebrae with little room for error in positioning the fixation screw.

Even as the cervical spine instrumentation techniques can be improved, so can the manner of fixation of the plate to the affected vertebral levels. For example, the Synthes, Inc. locking plate accepts spinal screws at several locations at the ends and in the middle of the plate. In each case, the screws are not capable of varying degrees of fixation between the vertebra and the plate. In addition, the Synthes device utilizes a locking screw which is threaded into the expansion head of the vertebral fixation screw to lock the screw into the plate. This procedure requires a locking screw for every fixation screw, thereby lengthening and complicating the procedure.

During anterior cervical surgery, alignment of the plate with the vertebral bodies and placement of the bone screws in the superior and inferior ends of the plate are often the most critical aspects of the procedure. The surgeon must securely and rigidly hold a bone plate against the anterior surface of the vertebral bodies, visualize the placement of the plate with fluoroscopy, obtain proper alignment, drill, tap and finally seat the bone screws. It is desirable to perform these steps using one instrument which firmly and consistently attaches to the plate in the stone manner every time.

There therefore remains a need for a cervical plating system which provides for a wider range of fixations at the different vertebral levels. The need also extends to a plating system which minimizes the steps required to provide firm fixation of the spinal screws to the plate. Other requirements for an optimum cervical fixation system addressed by the present invention are disclosed herein as the components of the system are described.

SUMMARY OF THE INVENTION

In accordance with one aspect of the invention, a system for anterior fixation of the spine includes an elongated fixation plate having a longitudinal axis and a length along the axis sufficient to span between at least two vertebrae. The plate includes a lower surface adapted to engage the anterior portion of the vertebrae and an opposite upper surface, as well as opposite first and second ends. A pair of screw bores are defined at both of the first and second ends between the lower and upper surfaces and displaced from each other transverse to the longitudinal axis of the plate. The pair of screw bores have centerlines that diverge relative to each other and relative to the lower surface of the plate. The system also includes several bone engaging screws, one each for each of the pair of screw bores at both of the first and second ends. Each of the screws includes em elongated shank with bone engaging threads and an enlarged head for engaging a corresponding one of the screw bores at the upper surface of the plate when the shank extends therethrough.

The divergent screw bores achieve one object of the invention to minimize the intrusion and trauma to tissue surrounding the implantation site. As the bores diverge below the plate, they converge above the plate so that two screws can be inserted through the bores at an end of the plate from essentially the same location. This improvement reduces the amount of tissue that must be retracted in order to provide access to the screw bores in the fixation plate. In one specific embodiment, the the centerlines of the pair of screw bores diverge relative to each other at an angle of about ten (10) degrees.

In a further aspect of the invention, the lower surface of the plate is curved transverse to the longitudinal axis to conform to the anterior surface of a vertebra and is curved along the longitudinal axis to conform to the lordotic curvature between the vertebrae. This feature eliminates having to bend the fixation plate at the surgical site during the instrumentation procedure.

To enhance the versatility of the spinal fixation system of the present invention, the fixation plate includes a number of elongated slots defined in the plate between the lower and upper surfaces disposed longitudinally between the number of screw bores at both ends of the plate. Each of the number of elongated slots has mutually parallel slot axes along their length that intersect the longitudinal axis of the plate at an acute angle. Additional bone engaging screws are provided for engaging intermediate vertebrae through one of the elongated slots. Preferably, the slots are arranged on the plate such that the ends of adjacent slots overlap each other transverse to the longitudinal axis of the plate.

One important component of the preferred embodiment of the invention is screw fixation means for clamping the head of the bone screws to the plate. Pursuant to this invention, the screw fixation means engaging the plate at its upper surface to clamp the bone screw heads within recesses in the plate. Preferably, the bone screws and the screw fixation means are configured to reside within recesses in the plate so that these components are flush with or below the upper surface of the plate. This aspect realizes an advantage over prior systems which include components projecting above the fixation plate, leading to irritation and trauma of the surrounding tissue.

In one specific embodiment, the screw fixation means includes a fixation bore defined in the plate at each of the first and second ends between the screw bores. A locking screw is provided having a shank adapted to be received within the fixation bore and an enlarged head adapted to simultaneously cover a portion of the head of both screws received within the pair of screw bores. In another embodiment, the screw fixation means contemplates screw bores and screw shanks that are complementary tapered at a MORSE TM taper. The integration of the MORSE TM taper enhances the degree of fixation between screw and plate, particularly when combined with the locking screw.

Still another embodiment of the screw fixation means is contemplated that includes a groove formed in the screw bores at the lower surface of the plate. The bone engaging screws include a corresponding groove defined in the shank of the screw between the head of the screw and the bone engaging threads. An O-ring is provided that has an outer diameter adapted to be retained within the groove in the plate and an inner diameter adapted to be retained within the groove in the shank of the bone screws. When the bone screw is mounted within the screw bore, the O-ring retains each of the bone screws within the bore without the necessity of a locking screw. However, the degree of rigidity of this fixation is less than the rigidity provided by the locking screw approach outlined above.

The invention further concerns an improved system for separately drilling fixation holes into vertebrae to be instrumented with a spinal plate. In one specific embodiment, the system includes a spinal plate with a number of screw bores adapted to receive spinal screws therethrough. A pin bore is also defined through the plate adjacent each of the number of screw bores. A drill guide is provided which includes a guide body having a lower surface configured for juxtaposition with the upper surface of the spinal plate and defining a guide bore and a second pin bore therethrough. The guide bore and the second pin bore are arranged to align with one of the number of screw bores and the pin bore, respectively, in the spinal plate when the guide body is juxtaposed with the plate.

The system further includes a pin adapted to be received between the spinal plate and the guide body within the pin bore and the second pin bore, respectively. The pin is rigidly engaged at one end to the guide body and at the opposite end to the spinal plate to accurately position and retain the guide body relative to the plate. An elongated sleeve having one end configured to be received within the guide bore of the guide body, and a drill bore therethrough is provided for integrating into the guide body. An elongated drill extends through the drill bore of the elongated sleeve.

In another embodiment the system includes a guide apparatus for holding a spinal plate and drilling and tapping the bone. The guide comprises two arms which pivot with respect to each other, a handle and two feet attached to the ends of the arms. Each foot has a hook integrally attached to the edge of the foot which is adapted to securely grasp a spinal plate. Each foot also has a pair of thru-holes. Each hole corresponds to screw bores in a spinal plate when the guide assembly is attached to a spinal plate. The system further includes a number of double-headed fixation pins. The diameter of the first head is greater than the diameter of the thru-holes in the feet. The diameter of the second head is smaller than the thru-holes but greater than the screw bores in the spinal plate. The fixation pins serve to hold the plate in position against the cervical spine during fluoroscopy and drilling and tapping. The system also contains a drill-tap sleeve having a stop member. The outside diameter or the sleeve is slightly smaller than the through holes in the feet. The system is intended to be used with a drill bit having a stop member.

The present invention provides many advantages and benefits over prior art anterior plating systems. One benefit is that the plating system of this invention minimizes the amount of intrusion at the instrumentation site. Another advantage is achieved by the reduced number of components required to achieve rigid fixation of the bone screws to bone and plate.

A further benefit resides in the smooth outer contour of the instrumentation once they are implanted that is accomplished by plate recesses and other aspects of the invention. The bone screws and screw fixation means are safely retained flush with or below the surface of the plate to remove this potential source for irritation and trauma to the surrounding tissue.

Other benefits, advantages and objects of this invention will become apparent to a person of skill in the field of spinal instrumentation upon consideration of the following written description and accompanying figures.

FIG. 14 is a front cross-sectional view of the plate holder-drill guide assembly.

DESCRIPTION OF THE PREFERRED EMBODIMENTS

Figure 1:
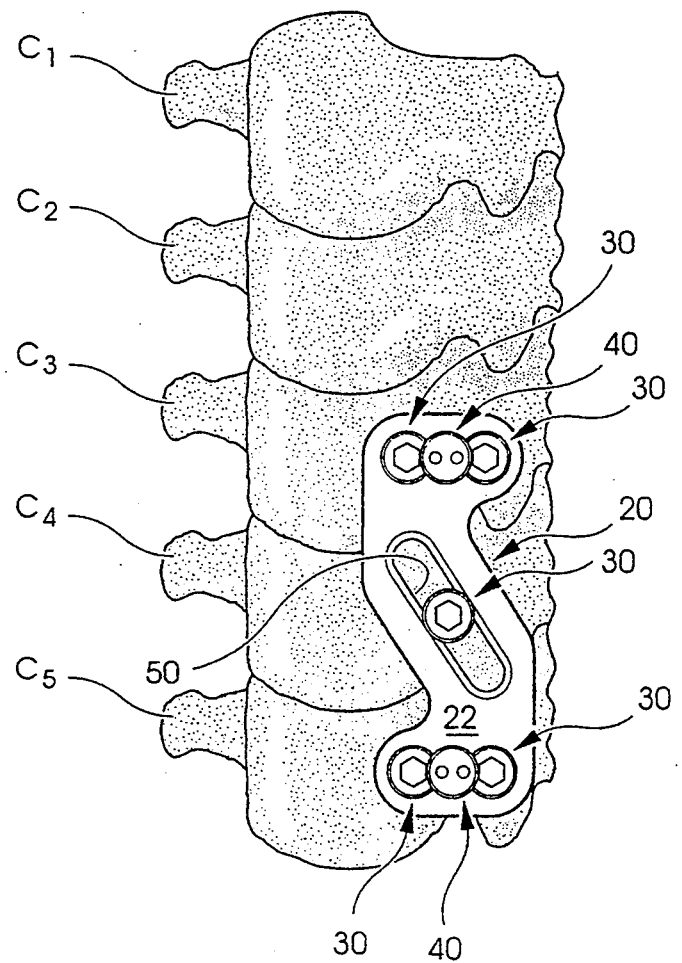
FIG. 1 is a representation of the upper cervical spine instrumented with the cervical plating system in accordance with one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In accordance with one embodiment of the invention, an elongated fixation plate 20 is instrumented to upper cervical vertebrae $C_1$-$C_4$, in particular between the $C_3$ and $C_5$ vertebrae. Such an arrangement may arise where the $C_4$ vertebrae requires fusion or to address a problem with the discs between these vertebrae. It is understood, of course, that while FIG. 1 depicts instrumentation between the $C_3$ and $C_5$ vertebrae, instrumentation at other vertebral levels is contemplated by the present invention. By general introduction to the components of the inventive system, the fixation plate 20 is engaged to the various vertebrae by way of a number of bone engaging screws 30. Screw fixation means 40 is provided to firmly and rigidly fix certain of the bone engaging screws to the plate.

Figure 2:
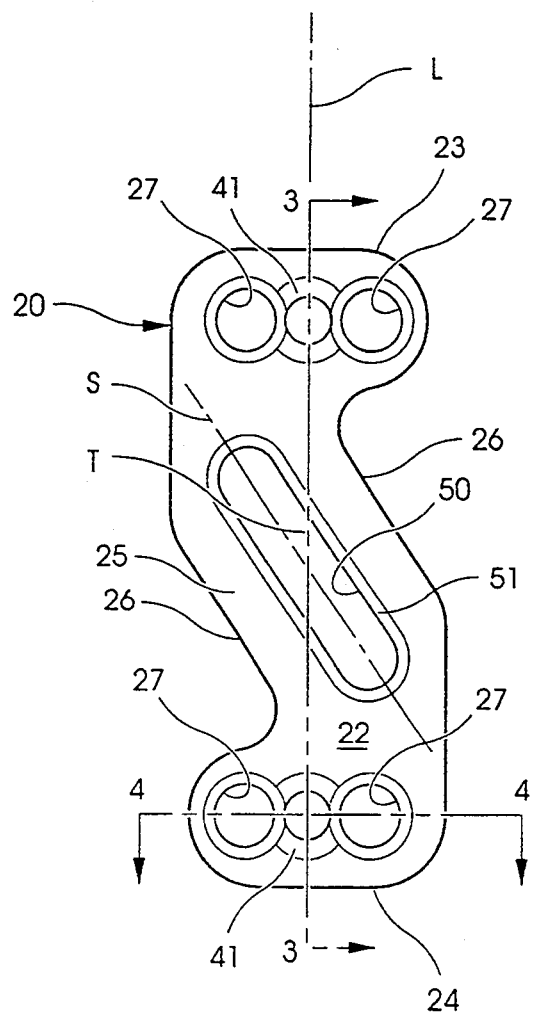
FIG. 2 is a top elevational view of a cervical plate in accordance with one embodiment of the invention as depicted in FIG. 1.
Figure 3:
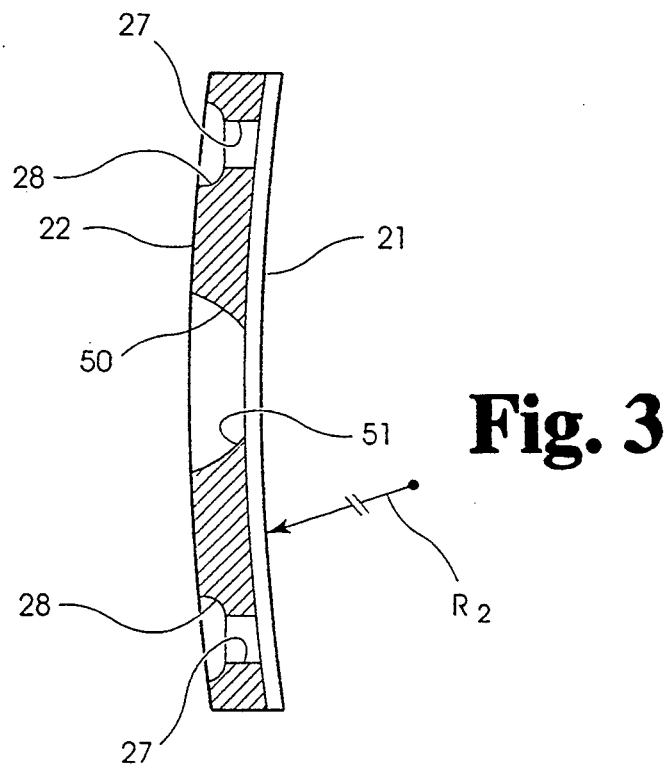
FIG. 3 is a side cross-sectional view of the plate shown in FIG. 2 taken along line 3—3 as viewed in the direction of the arrows.
Figure 4:
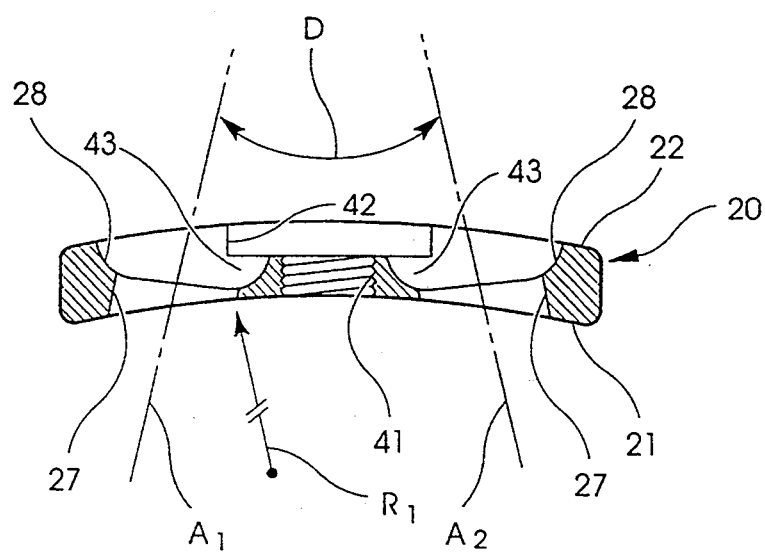
FIG. 4 is an end cross-sectional view of the plate shown in FIG. 2 taken along line 4—4 as viewed in the direction of the arrows.

Referring now to FIGS. 2–4, details of the construction of fixation plate 20 can be discerned. The plate 20 includes a lower surface 21 which is oriented adjacent the vertebra, and an opposite upper surface 22, as well as a first end 23 and an opposite second end 24. A bridge portion 25 spans between the two ends of the plate.

The plate 20 or the present embodiment includes a number of screw bores 27 defined in the plate. In the preferred embodiment, two screw bores are oriented at each of the first end 23 and the second end 24. Thus, four such screw bores are included so that fixation screws mounted in the plate through these bores provide a solid quadrilateral fixation to the instrumented vertebrae. Each of the bores 27 includes a spherically shaped recess 28 defined from the upper surface 22 of the plate, as shown more clearly in FIG. 4. As discussed in more detail herein, the recess 28 is adapted to receive and substantially conceal the head of a fixation screw extending through the bore.

Referring again to FIG. 4, it can be seen that the screw bores 27 at one end of the plate, such as end 24, are each cut at axes $A_1$ and $A_2$. These axes converge above the upper surface 22 of the plate at an angle D, which provides a significant benefit over prior systems. In prior cervical fixation plates, the axis of the screw bores are generally perpendicular to the curved plate surface, as in the Synthes cervical plate. With the curvature of the plate, the axes of the screw bores at which the screws must be inserted are divergent relative to the vertebra. This means that more soft tissue must be retracted around the instrumentation site in order to allow the fixation screws to be passed through the screw bore and threaded into the vertebra. On the other hand, in accordance with this aspect of the present invention, the convergent angle D between the two screw bores 27 at each end of the plate provide for insertion of the fixation screws from generally the same location above the plate. In this instance, less soft tissue needs to be retracted in order to allow the surgeon to pass a fixation screw through the plate and into the vertebra. In one specific embodiment, the angle D between the screw bore axes $A_1$ and $A_2$ is about ten (10) degrees. It has been found that this angle provides adequate purchase for the screws into the vertebrae, while allowing streamlined entry of the screws at the implant site.

As shown more clearly in FIGS. 3 and 4, the plate 20 is formed to define specific curvature in two directions. As seen in FIG. 4, the lower surface 21 of the plate is curved about a radius R which corresponds to the curvature of the anterior surface of a vertebra. This form of curvature is generally known in the art, such as evidenced by the Synthes plate. For cervical vertebrae, a radius $R_1$ of about 3.80 mm (1.50 inches) is acceptable. However, in accordance with the present invention, the lower surface 21 of the fixation plate 20 is also curved along its length at a radius $R_2$, as shown in FIG. 3, to correspond to the lordotic curvature of the cervical spine. Plates such as the Synthes plate must be bent at the time of surgery, if at all. It has been found that forming the fixation plate 20 with the lordotic curvature radius $R_2$ in the lower surface 21 of the plate eliminates unnecessary activity by the surgeon during the procedure and reduces any bending stresses that may be inherent in the plate when it is bent at the surgical site. In cervical vertebra applications, a radius of about 18.4 mm (725 inches) accommodated the cervical lordotic curvature.

Figure 5:
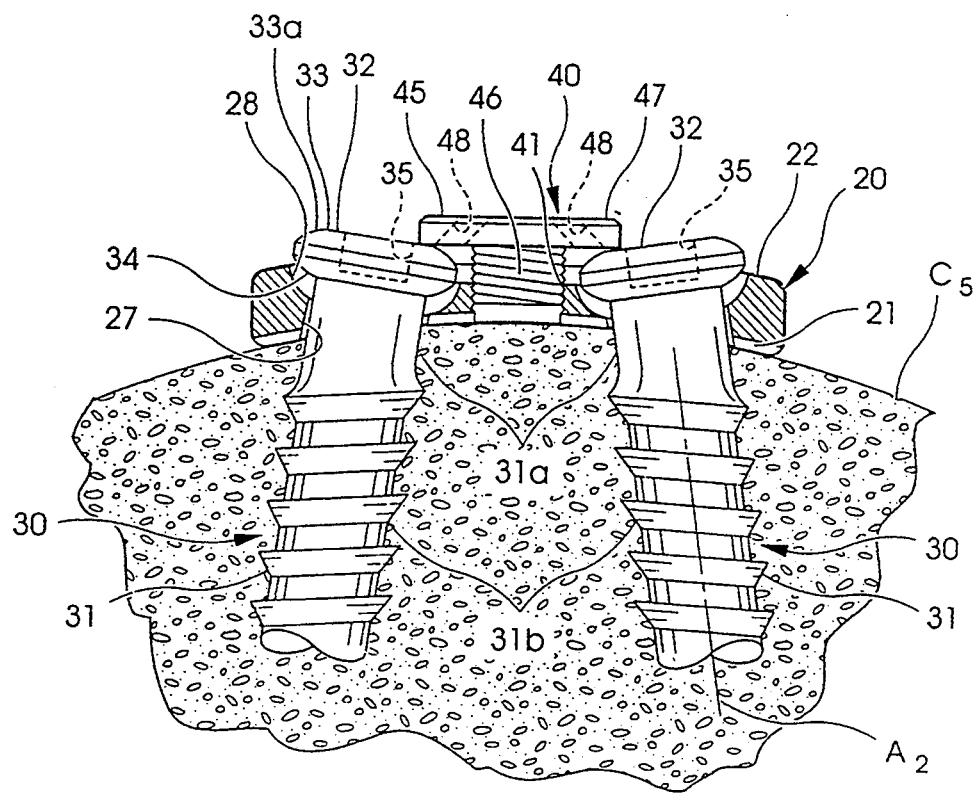
FIG. 5 is an end cross-sectional view of the plate, similar to the view in FIG. 4, showing the plating system with the fixation screws partially threaded into the vertebra just before being firmly affixed to the cervical plate.

Referring now to FIG. 5, the details of the bone engaging screws 30 and there interface with the fixation plate 20 are shown. Each bone engaging screw 30 includes an elongated shank 31 having a lower threaded portion 31b and an upper smooth portion 31a. Adjacent the smooth portion 31a is an enlarged head 32 of the screw. The head 32 includes a truncated spherical upper surface 33a and an opposite spherically cut lower surface 34. The lower surface 34 is curved to match the curvature of the spherical recess 28 of the screw bores 27 in the plate 20. The upper surface 33 is truncated to provide a flat face, and defines a driving tool recess 35 formed therein. The driving tool recess is adapted to engage a standard driving tool, such as an allen head tool frequently used to thread bone screws into a vertebra.

Figure 6:
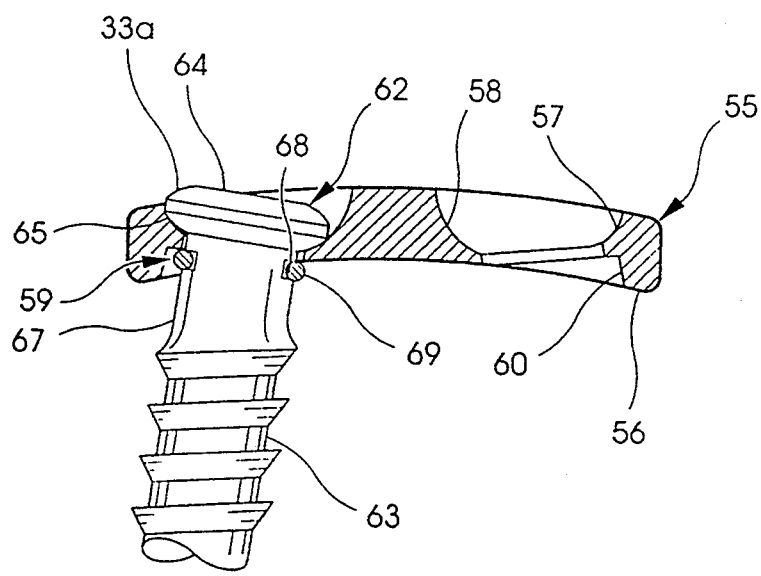
FIG. 6 is an end cross-sectional view similar to the view in FIG. 4 showing an alternative embodiment of the plate and fixation screw.

One important aspect of the screw 30 in accordance with the present invention resides in the configuration of the upper surface 33 of the head 32. The truncated spherical aspect of the head allows substantially the entire screw head 32 to rest entirely within the screw bore recess 28. In this manner, a portion of the screw head 32 is substantially flush with the upper surface 22 of the plate, while the remainder of the screw resides below the upper surface within the recess 28. In FIG. 5 the bone engaging screws 30 are shown just prior to being completely fixed within the fixation plate 20. FIG. 6, while showing an alternative embodiment of the bone screw, accurately depicts the flush mounted aspect of this invention. The particular angle of the screw bores axes $A_1$ and $A_2$ require a cutback of the top surface of the enlarged screw head 32. While in the preferred embodiment this upper surface is a truncated spherical surface 33a, it is contemplated that the head 32 can simply include beveled perimeter, provided that the cutback of the head 32 is sufficient to allow the head to be substantially flush or below the upper surface 22 of the fixation plate 20.

As with other cervical implant systems, the present invention contemplates some means for fixing the bone engaging screws 30 to the fixation plate 20 to prevent the screws from working loose over time. Consequently, the system includes a screw fixation means 40, depicted best in FIGS. 4 and 5. In one embodiment of the invention, the screw fixation means 40 includes a threaded fixation bore 41 formed in the plate 20 between the two screw bores 27 at each end of the plate. The fixation bore 41 includes a recessed bore 42 defined from the upper surface 22 of the plate, as shown more particularly in the cross-sectional view of FIG. 4.

As can be seen from FIGS. 2 and 4, the fixation bore 41, and particularly the recessed bore portion 42, share an overlap 43 with the screw bores 27. The necessity for this overlap is revealed in FIG. 5 which shows a second component of the fixation means 40, the locking screw 45. The locking screw 45 includes a threaded stem 46 which is configured to engage the threaded bore 41 in the plate 20. The locking screw 45 includes a flat head 47 which is thin enough to reside entirely within the recessed bore portion 42 in the plate so that the locking screw is not exposed above the upper surface 22 of the plate. The head 47 includes a pair of driving tool bores 48 which are configured to receive a pin type driving tool for threading the locking screw 45 into the fixation bore 41. Other configurations, such as an allen head recess, are contemplated to permit threading the locking screw 45 into the fixation bore 41.

The locking screw 45, particularly at the overlap 43, contacts each of the bone engaging screws 30 situated within the screw bores 27. Typically, the bone engaging screws 30 would already be threaded fully into the vertebra so that the lower head surfaces 34 of the screws are in direct contact with the spherical recess 28 of the plate. (The screws are shown slightly backed out in FIG. 5 to allow mode complete visualization of the features of this invention.) In addition, the lower surface 21 of the fixation plate 20 would normally be pressed to contact with the vertebra. In this configuration, the locking screw 45 is driven into the fixation bore 41 until the head 47 contacts and firmly clamps a portion of the head 32 of both bone engaging screws 30 at the overlap 43.

The addition of the fixation means 40 and locking screw 45 provides a means for rigidly fixing the bone engaging screws 30 to the fixation plate 20. Specifically, the bone engaging screws 30 are highly restricted in their ability to wobble or rotate within the recess 20 of the screw bore 27 when clamped by the locking screw 45. The screw fixation memos 40 of the present invention provides a unique method for fixing two bone engaging screws at one time. Prior techniques required individual means for fixing each screw separately, which complicated the procedure and added additional instrumentation to the implant. On the other hand, the fixation means 40 of the present invention greatly streamlines the process of rigidly fixing the bone engaging screws 30 to the plate 20. In accordance with a typical procedure, once the appropriate openings have been drilled and tapped into the vertebra, the plate 20 can be positioned against the vertebra and the bone engaging screws 30 be driven into the bone through the screw bores 27 in the plate. Once the screws 30 have been driven to the proper depth and torque the locking screw 45 of the screw fixation means 40 can be firmly threaded into the fixation bore 41 to clip the head 32 of each of the bone screws 30 within their respective recesses 28.

Attention is now redirected to FIGS. 1–3 for explanation of a further feature of the fixation plate 20 of the present invention. In accordance with one embodiment of the invention, the plate 20 includes a slot 50 formed within the bridge portion 25 of the plate. The slot 50 has a concave surface 51 formed like the spherical recesses 28 of the the screw bores 27 to accept the head 32 of a bone engaging screw 30 as previously described. In accordance with the invention, the slot 50, or the axis S along the length of the slot, is oriented at an acute angle T to the longitudinal axis L of the fixation plate 20. This diagonal slot 50 provides means for supporting an added bone screw between the two instrumented vertebrae fixed at the ends of the plate.

Unlike the bone engaging screws passing through the screw bores 27 at the ends of the plate 20, a screw extending through the diagonal slot 50 preferably does not include any means for rigidly fixing the head of the screw to the plate. Thus, only a "semi-rigid" fixation is provided between a screw within the slot 50 and the spanned vertebra. Although rigid fixation is essential at the ends of the plate to keep the plate firmly engaged to the vertebrae, non-rigid fixation of the intermediate screw passing through the slot 50 is all that is required and is in fact desired to avoid complications following the instrumentation of the vertebrae.

The orientation of the slot 50 at its acute angle T allows the bridge portion 25 of the plate to be cut back somewhat to reduce the incursion into surrounding tissue and the associated trauma. In particular, the sidewalls 26 of the bridge 25 can be cut parallel to the slot walls provided sufficient material is maintained to support the slot and prevent fracture of the plate at the slot. Similarly, sufficient material must be located around the screw bores 27 at the ends of the plate to provide a sufficiently strong plate. One object of the invention is to reduce the amount of trauma to surrounding tissue, as well as the amount of space required for the plate when it is affixed to vertebrae. Cutting the plate contours, such as the sidewalls 26 of the bridge portion 25, in the manner shown achieves these purposes, while also reducing the amount of material used to make the plate.

A further embodiment of the invention includes a fixation plate 55 illustrated in FIG. 6. The fixation plate 55 includes a lower surface 56 configured to contact the surface of a cervical vertebra. As with the fixation plate 20 of the previous embodiment, the plate 55 includes a pair of screw bores 57 at each end of the plate. Each screw bore 57 includes a spherical recess 58 adapted to receive a bone engaging screw similar to screw 30.

The fixation plate 55 differs from the previous plate 20 in the manner of fixing the bone engaging screws to the plate. In particular, the plate 55 does not include a locking screw 45 or fixation bore 41 as shown in FIG. 5. Instead, the screw fixation means 59 of this embodiment contemplates modifications to the bone screw and to the plate. Specifically, the fixation means 59 includes a lower circular recess 60 defined in the screw bore 57 at the lower surface 56 of the plate. A modified bone engaging screw 62 is provided which includes an elongated shank 63 having bone engaging threads. The head of the bone screw 64 is configured similar to the head 32 of the bone engaging screws 30 so that the screw can be situated flush with or below the upper surface of the fixation plate 55, with the lower surface 65 of the head 64 in contact with the spherical recess 58.

The bone engaging screw 62 includes a smooth shank portion 67 between the threaded shank 63 and the head 64. A groove 68 is defined in the smooth shank portion 67 immediately below the screw head 64. The groove 68 is configured to receive an O-ring 69 which is trapped between the groove 68 and the lower recess 60 in the fixation plate 55. Preferably, the O-ring is formed of a biocompatible elastomeric material that is strong enough to resist screw pull out. In particular, any outward movement of the bone screw is resisted by the pressure transmitted between the recess 60 and the groove 68 and the bone screw through the O-ring 69.

Figure 7:
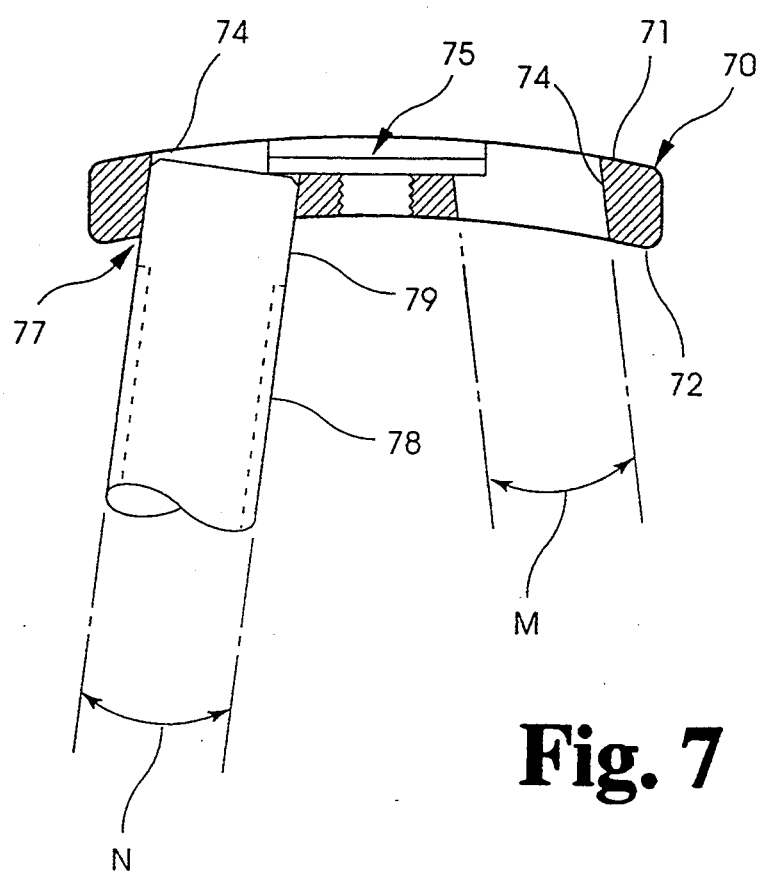
FIG. 7 is an end cross-sectional view similar to FIG. 4 showing yet another embodiment of the plate and fixation screw of the present invention.

Yet another embodiment of the cervical fixation plate is shown in FIG. 7. In this embodiment, a fixation plate 70 includes an upper surface 71 and an opposite lower surface 72. A pair of screw bores 74 are defined through the plates at the same angles as the bores 27 in the embodiment shown in FIGS. 1–4. In addition like the embodiment shown in FIG. 5, a screw fixation means 75 incorporating a locking screw is included to help clamp the bone screw to the plate. However, in a modification from the previous embodiments, the screw bore 74 is tapered at an included angle M. This taper M converges from the upper surface 71 to the lower surface 72. Also included in this embodiment is a bone engaging screw 77 which tapers at an included angle N. The two angles M and N are MORSE TM taper angles of preferably 2–3 degrees. This MORSE TM taper angles are known in machine design to form a tight engagement between components when both are cut at a MORSE TM angle. The bone engaging screw 77 includes a threaded portion 78 and head portion 79. At least the head portion 79 of the bone engaging screw 77 is tapered at the MORSE TM taper N to firmly fix within the MORSE TM taper M of the screw bore 74. The interface between the two MORSE TM tapers add a higher degree of fixation of the bone engaging screw 77, particularly when combined with the screw fixation means 75.

Figure 8:
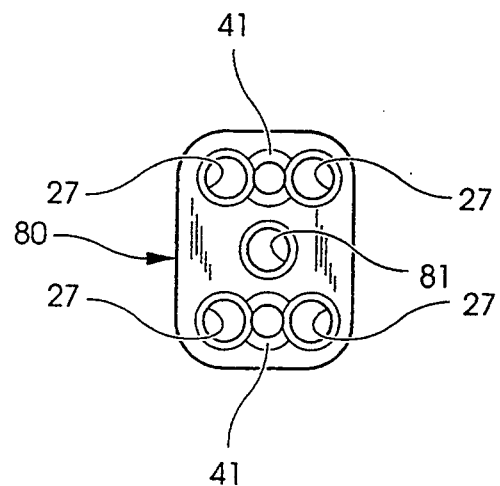
FIG. 8 is a top elevational view of an alternative embodiment of the fixation plate.
Figure 9:
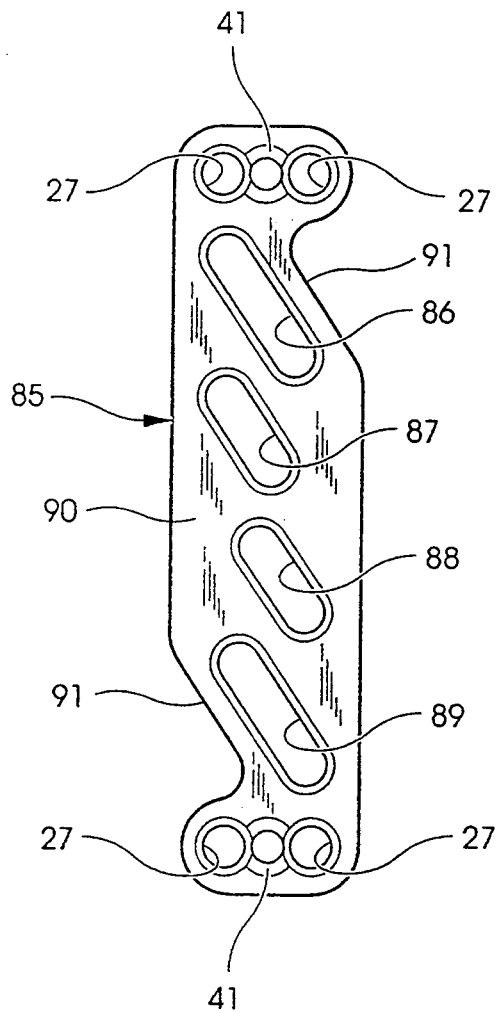
FIG. 9 is a top elevational view of still another alternative embodiment of the fixation plate in accordance with the present invention.

In order to provide a broad range of plates for fixing to the cervical vertebra to address a variety of spinal problems, a number of different spinal plates can be provided with a complete cervical fixation system. Two such alternative plates are shown in FIGS. 8 and 9. The first plate 80 is a nearly square plate having the two screw bores 27 at the opposite ends of the plate along with the fixation bore 41 to receive a screw fixation means 40 as previously described. However, in this embodiment, the slot 50 of the previous plate is eliminated in favor of a single bore 81. This single bore does not allow the variability of position of the fixation screw relative to the rigid fixation screws, but it does provide means for a non-rigid engagement to the plate.

The fixation plate 85 shown in FIG. 9 is substantially like the plate 20 shown in FIG. 1 with the addition of several parallel slots. Specifically, slots 86–89 are included in the bridge portion 90 of the plate. Again as with the plate 20, the sidewalls 21 of the bridge portion 90 are cut at the slot angle to achieve the functions described above. With the plate 85 of this embodiment of the invention, a number of slots allow the fixation plate to span across a number of cervical vertebrae. The ends of each successive plate laterally overlap so that a single intermediate vertebra can be instrumented with two bone screws extending through two different slots, such as consecutive slots 86 and 87. As also seen in FIG. 9, the length of the slots 86 and 89 is greater than the length of slots 87 and 88, principally because the slots 87 and 88 are situated within the middle of the bridge portion 90. In order to allow sufficient material around the slots, the middle of slots 87 and 88 cannot have the same length as the end slots 86 and 87.

Also included with the cervical plating system of the invention is a drill and tap guide assembly 100, the details of which are described in connection with FIGS. 10–13. It should first be appreciated that in typical prior art systems the fixation plate itself serves as the guide for drilling the hole locations in the vertebra to receive the fixation screws. Currently, no instruments or procedure exists which allows the surgeon to securely and rigidly hold an anterior cervical plate against the anterior surface of the vertebral bodies, utilize fluoroscopy, obtain proper alignment, drill, tap and finally seat the bone screws all utilizing the same instrument without this instrument being removed until all implantation steps are complete. For example, in the Synthes cervical spine plating system, a plate positioner holds the plate in position on the vertebra while each screw hole is being drilled. A soft tissue protector is provided which surrounds the drill and which is seated within the screw bores in the plate. Consequently since a portion of the tissue protector sheath is situated within the screw bore, the diameter of the drill and tap that can pass through the bore must necessarily be noticeably smaller than the bore itself. This means that the tap hole in the bone is smaller than the bone screw to be fixed into the vertebra, rendering threading the bone screw more difficult than if the tap were closer to the diameter of the bone screw itself. The drill and tap guide assembly 100 of the present invention eliminates this difficulty. In addition, the tap guide provides for virtually error free positioning of the drill and tap holes in the vertebra, which cannot be readily accomplished by the essentially cantilevered supported soft tissue retractor sheath in the prior art devices. The drill and tap guide assembly 100 includes several components, such as the assembly support 101, the sleeve 102, the drill guide 103, the drill 104, a positioning screw 105 and cross pins 106.

The assembly support 101 includes a guide body 110 which is a substantially solid block with a contoured lowered surface 111 adapted to fit the contour of the upper surface 22 of a fixation plate 20, (such as the plate shown in FIG. 1). The guide body 110 includes an integral flange 113 extending beyond one side and bottom edge of the body. In particular, the flange 113 is adapted to engage an end face 24 of the plate 20, as shown more particularly in FIG. 13. This flange 113 assists in properly positively positioning the drill guide assembly 100 relative to the plate 20 and the vertebra. The guide body 110 includes a pair of guide bores 115 and 116, which bores are lined to coincide with the axes $A_1$ and $A_2$ of the fixation screw bores 27 in the plate 20. Thus, with the guide body 110 resting on top of the upper surface 22 of the plate, the two guide bores 115 and 116 should substantially align and coincide with the fixation screw bores 27 at one end of the plate 20.

Figure 10:
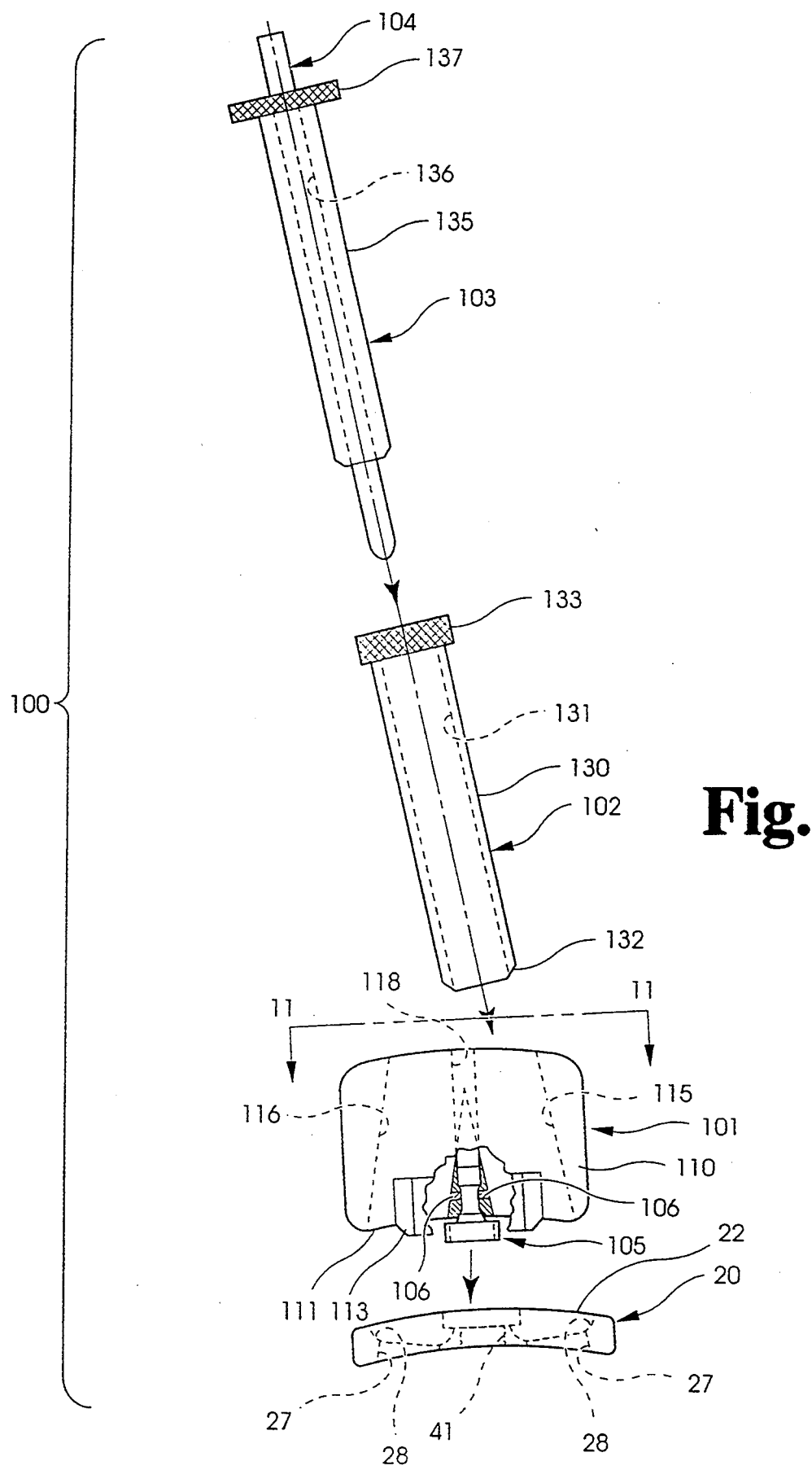
FIG. 10 is an exploded view of a drill and tap guide assembly in accordance with the present invention used in connection with the fixation plates of the previous figures.
Figure 11:
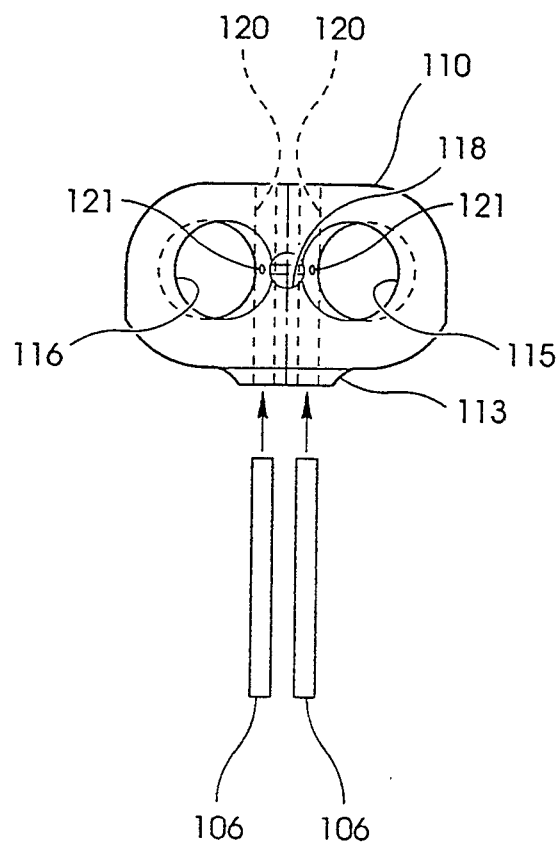
FIG. 11 is a top view of the assembly support of the drill and tap guide assembly shown in FIG. 10, as viewed in the direction of the arrows on line 11—11, in which the cross pins are shown prior to insertion into the assembly support.
Figure 12:
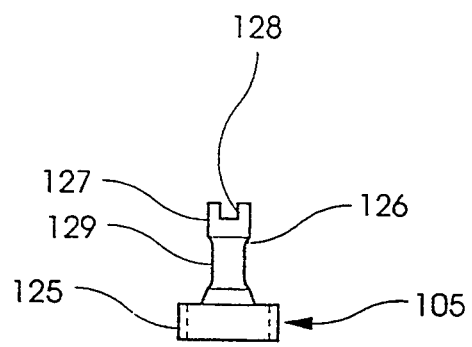
FIG. 12 is a side elevational view of the positioning screw shown in FIG. 10.
Figure 13:
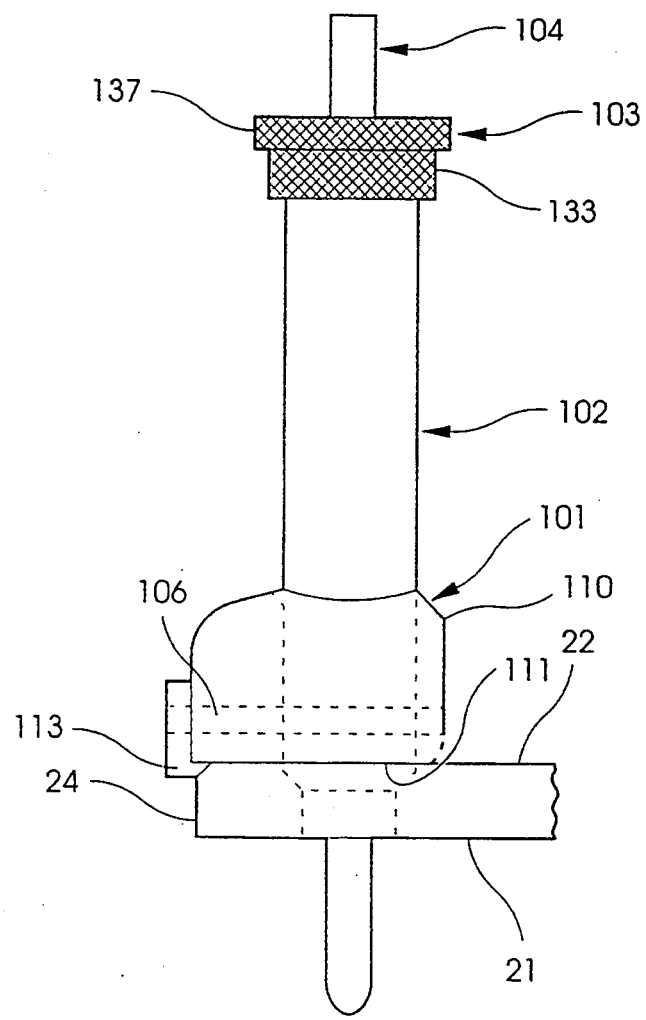
FIG. 13 is a side elevational view of the drill and tap guide assembly as arranged during a typical drill and tap operation.

The guide body 110 is engaged to the plate 20 in a unique fashion. For this engagement, the guide body includes a positioning screw bore 118 which is centrally located between the two converging guide bores 115 and 116. The positioning screw bore 118 is adapted to receive a portion of a positioning screw 105 therein. The details of the positioning screw are shown in FIG. 12. In the preferred embodiment, the positioning screw 105 includes a head 125 which is threaded to to engage the threaded fixation bore 41 in the plate 20. (The fixation bore 41 is used also for engaging the locking screw 45 as part of the screw fixation means 40, as described above). Extending from the threaded head 125 is a stem 126 which has a driving tip 127 at its end. The driving tip includes a transverse slot 128 that is adapted to receive a driving instrument, such as a screwdriver to allow the threaded head 125 to be screwed into the fixation bore 41 of the plate 20. The positioning screw further includes a contoured portion 129 of the stem which is adapted to provide a locking surface for cross pins 106. As shown in FIGS. 10 and 11, cross pins 106 are extended through cross pin bores 120 which pass perpendicularly to the positioning screw bore 118. The cross pins bores overlap both with the positioning screw bore 118 and a corresponding one of the guide bores 115 or 116, such as shown in the overlap 121 in FIG. 11.

The importance of these various components can be appreciated by description of the manner in which the assembly support 101 is affixed to the fixation plate 20. In particular, in one manner of using the assembly support, the threaded head 125 of the positioning screw 105 is threaded into the fixation bore 41 of the plate 20 with the stem 126 projecting upward away from the top surface 22 of the plate. The positioning screw 105 is initially loosely threaded into the bore. The guide body 110 is then placed over the positioning screw 105 with the screw extending through the positioning screw bore 118 in the center of the body. The flange 113 helps locate the guide body 110 with respect to the edge 24 of the plate, and more particularly with respect to the screw bores 27 at the end of the plate. With the guide body 110 mounted over the positioning screw 105, the cross pins 106 are pushed through the cross pin bores 120 on either side of the positioning screw 105. The cross pins thus contact the contoured portion 129 of the positioning screw stem 126. The guide body 110 is then at least initially connected to the plate 20 by way of the positioning screw 105 and the cross pins 106 which engage the positioning screw. At this stage, however, the engagement between the guide body 110 and the plate 20 is not tight, awaiting the next step for completing the drill and tap guide assembly 100. The positioning screw bore 118 allows access for a driving tool to engage the driving tip 127, and particularly the slot 128, of the positioning screw 105, to tightly thread the screw into the threaded bore 41 when the assembly is complete.

The assembly 100 further includes a tap sleeve 102 that includes a sleeve body 130 defining a drill guide bore 131 therethrough. At one end of the sleeve body 130 is an end taper 132, which can be generally configured to engage the spherical recess 28 of the screw bore 27 in the plate 20. The other end of the sleeve body 130 includes an enlarged stop 133. Nominally, the sleeve body 130 has a diameter slightly smaller than one of the guide bores 115 or 116, while the stop 133 has a diameter larger than these bores. With the addition of the tap sleeve 102, the engagement between the assembly support 101 and the plate 20 can be completed. Once the guide body 110 is preliminarily positioned and attached to the plate by way of the positioning screw 105 and cross pins 120, the sleeve body 130 can be passed through one of the guide bores, such as guide bore 115, until the tapered end 132 of the sleeve body 130 contacts the spherical recess 28 in the plate 20. As the sleeve body 130 passes through the bore 115, the outer surface of the sleeve presses against one of the cross pins 106, which cross pin firmly presses against the stem portion 129 of the positioning screw 105. This provides a solid engagement of all of the components of the drill and tap guide assembly extending from the tap sleeve 102 to the plate 20. While the cross pin 106 presses against the positioning screw 105, it also presses back against the sleeve body 130 to provide some clamping force to hold the sleeve within the guide body 110.

With these components of the drill and tap guide assembly 100 firmly engaged, it is now possible to pass the drill guide 103 through the bore 131 in the tap sleeve body 130. The drill guide body 135 includes a drill bore 136 adapted to receive the drill 104 therethrough. The body 135 also includes a stop 137 which is larger than the drill guide bore 131 in the tap sleeve body 130, to prevent the drill guide from passing completely through the tap sleeve body. The final arrangement of the components is shown in the side view of FIG. 13. In this view it can be appreciated that the flange 113 helps locate the guide body 110 relative to the plate so the drill bores 131 and screw bores 27 align. The guide body 110, when fixed to the plate 20 by the positioning screw 105 and cross pins 106, provides a solid and accurate location for the tap sleeve 102, the drill guide 103 nested within the tap sleeve, and ultimately the drill 104 passing through each of these components. It can certainly be appreciated that the drill and tap guide assembly 100 of the present invention provides a firm foundation and accurate location for drilling and tapping holes in the vertebra at the proper location relative to the fixation plate 20. The assembly 100 of the present invention still utilizes the fixation plate 20 as a template for locating the screw holes. However, the assembly 100 provides a firmer foundation for performing the drilling and tapping operation than any known prior art device.

Figure 18:
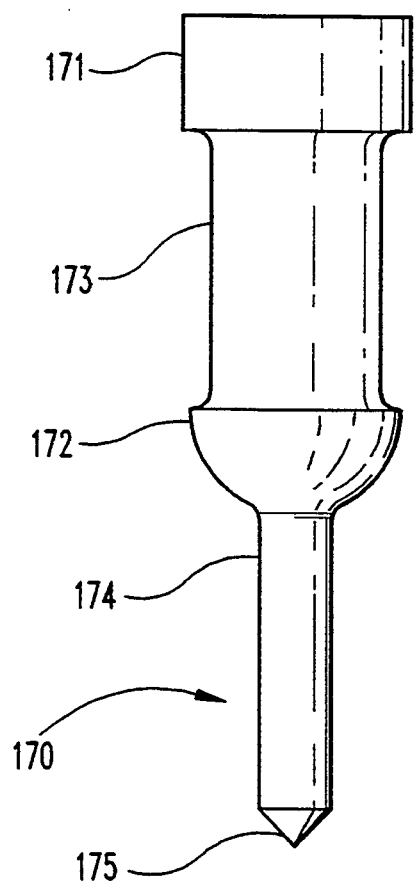
FIG. 18 is a side cross-sectional view of the double-headed pin.
Figure 19:
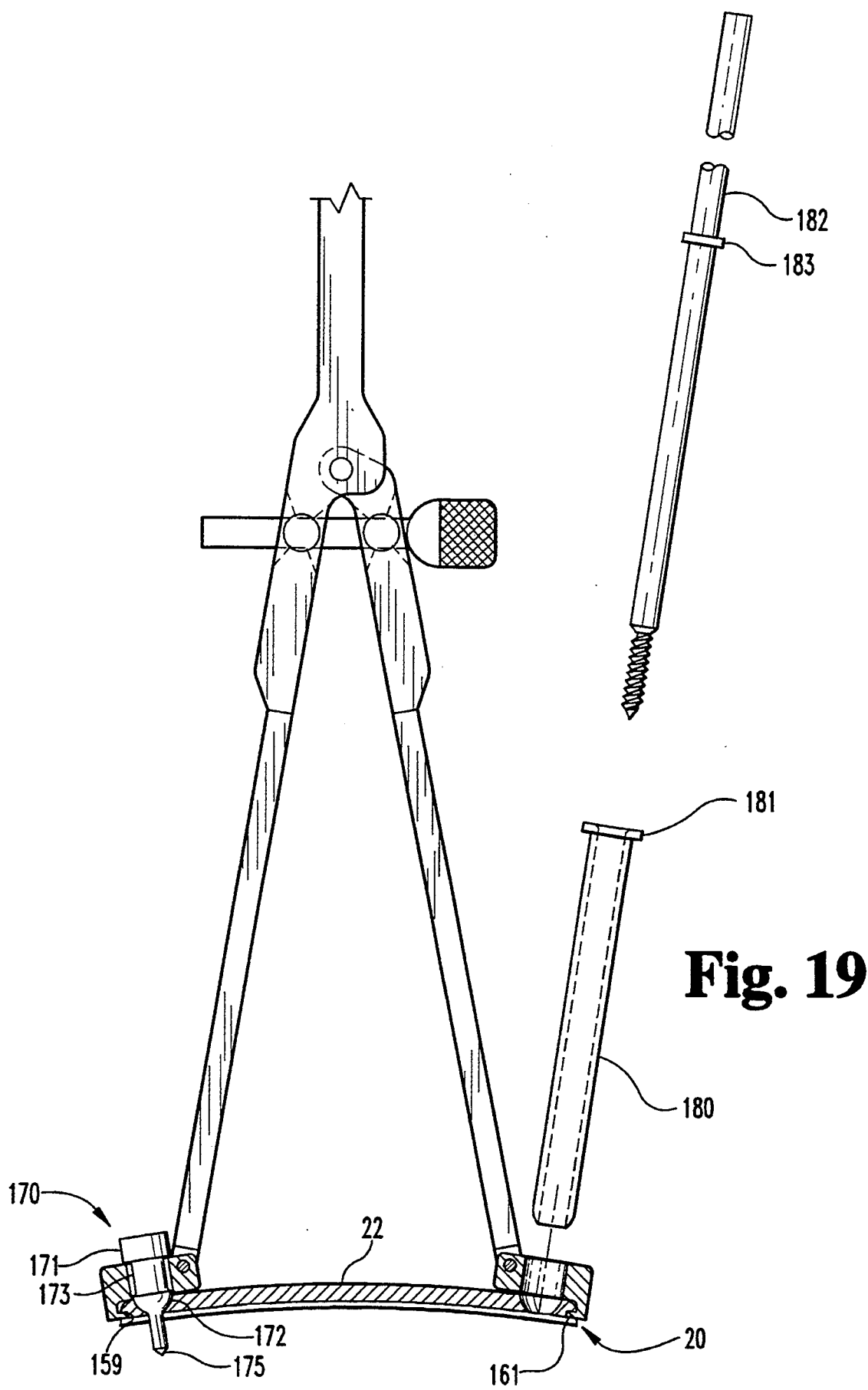
FIG. 19 is an exploded view of a guide assembly in accordance with the present invention used in connection with the fixation plates of the previous figures.

A further embodiment of the invention is shown in FIGS. 14–19. In this embodiment, the system includes a holder-drill guide 150, double-headed fixation pins 170, a drill-tap sleeve 180 having a stop member 181, a drill bit 182 having a stop member 183, a bone screw tap (not shown), bone screws 30 and a bone plate 20. The guide includes two feet 157, two arms 151, 152, a locking mechanism 153 and a handle 162. Each foot defines a pair of thru-holes 158 which are aligned with the screw bores 27 when the bone plate 20 is engaged to the guide 150. A small hook 161 on each foot 157 of the guide attaches to a notch 159 on each end of the plate 20. The locking mechanism 153 is then tightened to firmly attach the guide 150 to the plate 20. Double-headed fixation pins 170, as shown in FIG. 18, are provided to temporarily attach the entire guide-plate assembly to the bone. The pins 170 include a first head 171, having a diameter larger than the diameter of the thru-holes 158 of the feet 157, a second head 172 having a diameter smaller than the diameter of the thru-holes 158 but larger than the screw bore 27 in the plate 20. The first head 171 and the second head 172 are connected by a neck portion 173. The fixation pins 170 also include a shaft 174 attached to the second head 172 and tapering to a point 175. Referring to FIG. 19, the first head 171 of the pin 170 sits above the foot 157, while the neck portion 173 extends through the thru-hole 158, the second head 172 rests in the spherical recess 28 and the shaft 174 and pointed portion 175 extend through the screw bore 27 and into the bone. One pin 170 will be placed in one of the two holes 158 in each foot 157 of the guide, thus holding the plate 20 in position against the cervical spine while final positioning can be verified with fluoroscopy.

Referring to FIG. 19, a screw is seated in each unused screw bore 27 in both ends 23, 24 of the plate 20 in this manner: The drill-tap sleeve 180 is placed in the unused hole in each end of the guide 150. A drill bit 182 with stop 183 is then used through the sleeve 180 followed by a bone screw tap with a stop (not shown). The sleeve 180 is then removed and a bone screw 30 is placed through the same hole in the foot 157 of the guide 150. After the screw 30 is tightened down, it rests in the spherical recess 28 in the end 23, 24 of the plate 20.

After one bone screw 30 is placed in each end 23, 24 of the plate 20, the fixation pins 170 are removed and a sleeve 180 is placed in each of these holes, and the process is repeated until two screws 30 are firmly attaching each end of the plate 20 to the cervical spine. At this point, the locking mechanism 153 is loosened and the guide 150 is removed.

It is important to note that this guide can be made adjustable to cover a wide range of plate lengths. The arms 151, 152 of the guide 150 are pivotally attached to each other by way of a pivot bolt 160. The degree of the angle formed by the two arms 151, 152 is adjusted by a locking mechanism 153. The locking mechanism 153 includes a locking rod 155, pivot pins 156 and an adjustment knob 154.

Figure 17:
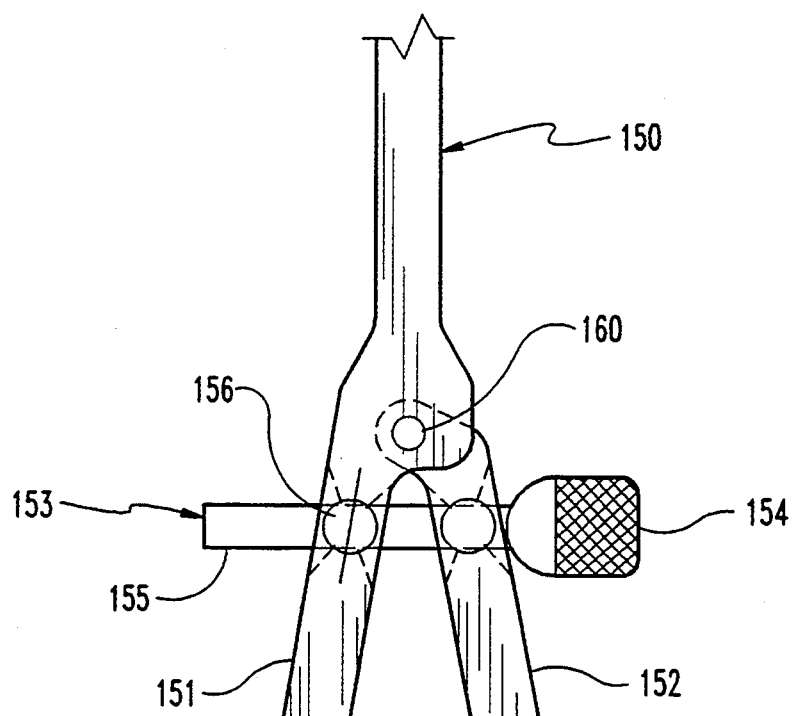
FIG. 17 is a elevational view of the holder engaged to a bone plate.
Figure 17:
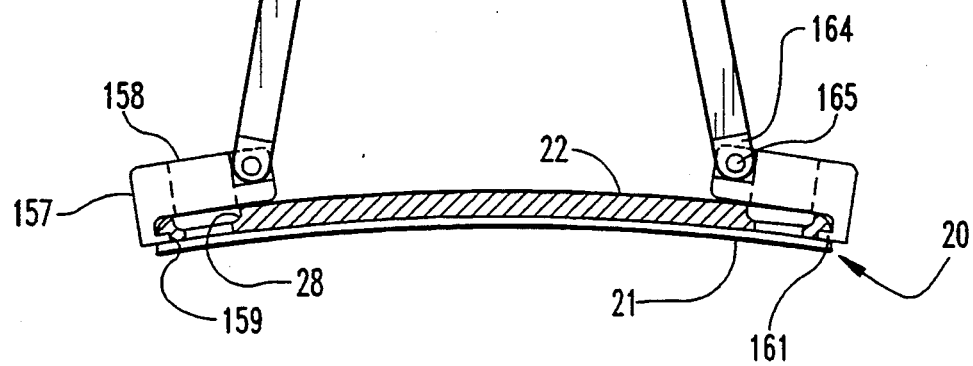

Referring now to FIGS. 14 and 17, the locking rod 155 extends through the pivot pins 156. The locking rod 155 is provided with an external threaded surface and the pivot pins 156 are provided with a mating internal threaded surface. The threaded surfaces mesh so that when the locking rod 155 is turned by way of the adjustment knob 154, the turning action of the locking rod 155 pushes the two pivot pins 156 in opposite directions thereby increasing or decreasing the angle between the arms 151, 152, and providing or relieving a clamping force on the plate 20.

Figure 15:
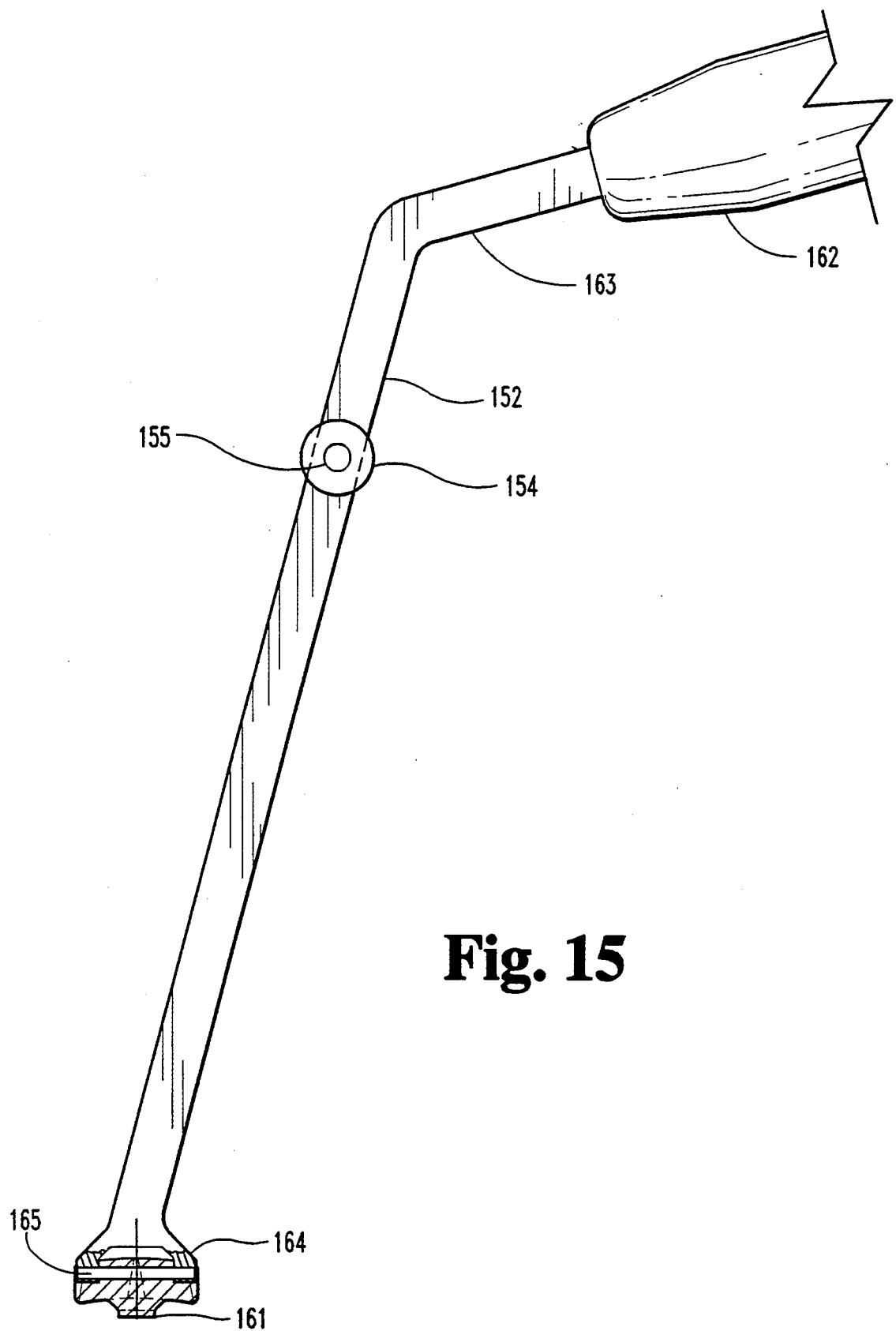
FIG. 15 is a side cross-sectional view of the guide assembly.
Figure 16:
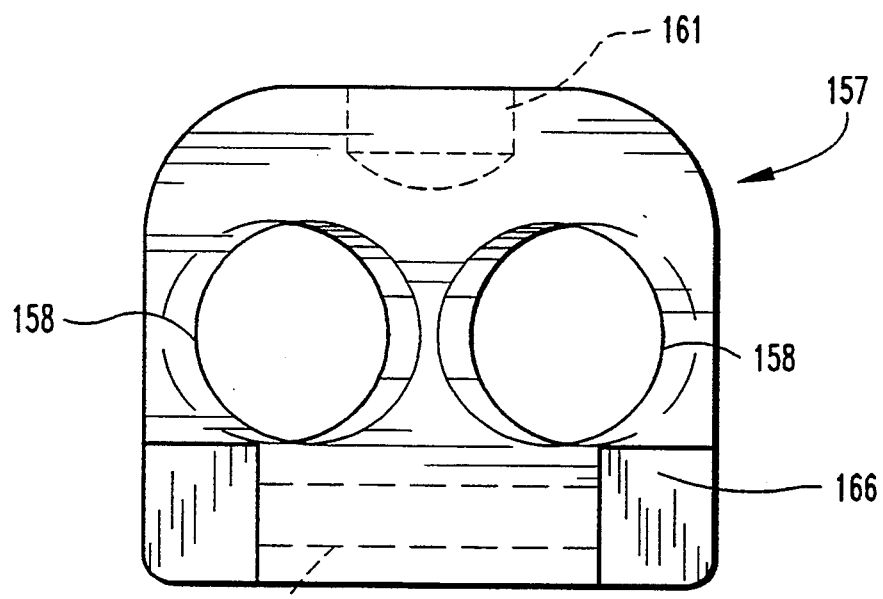
FIG. 16 is a top view of the feet shown in FIG. 14, as viewed in the direction of the arrows on line 16—16.

Referring now to FIG. 16 each foot 157 defines two cut out attachment points 166. Each arm 151, 152 is provided with two attachment fingers 164, as shown in FIGS. 14 and 15 which are attached to the attachment points 166 of each foot 157 by way of a dowel 165. The feet 157 are thus pivotally attached to the arms 151, 152 to adapt to plates 20 of various lengths and curvatures.

FIG. 19 shows a drill bit 182 and drill sleeve 180. A bone tap (not shown) would also fit through the sleeve 180 to prepare the drilled hole for the bone screw 30. This sleeve 180 must be removed for the bone screw 30 to fit through the foot 157 of the guide 150 although the system could be designed such that the bone screw 30 and screwdriver themselves also fit through the sleeve 180. This would mean the sleeve 180 would not be removed until the bone screws 30 have been firmly affixed to the plate 20 and bone.

Figure 20:
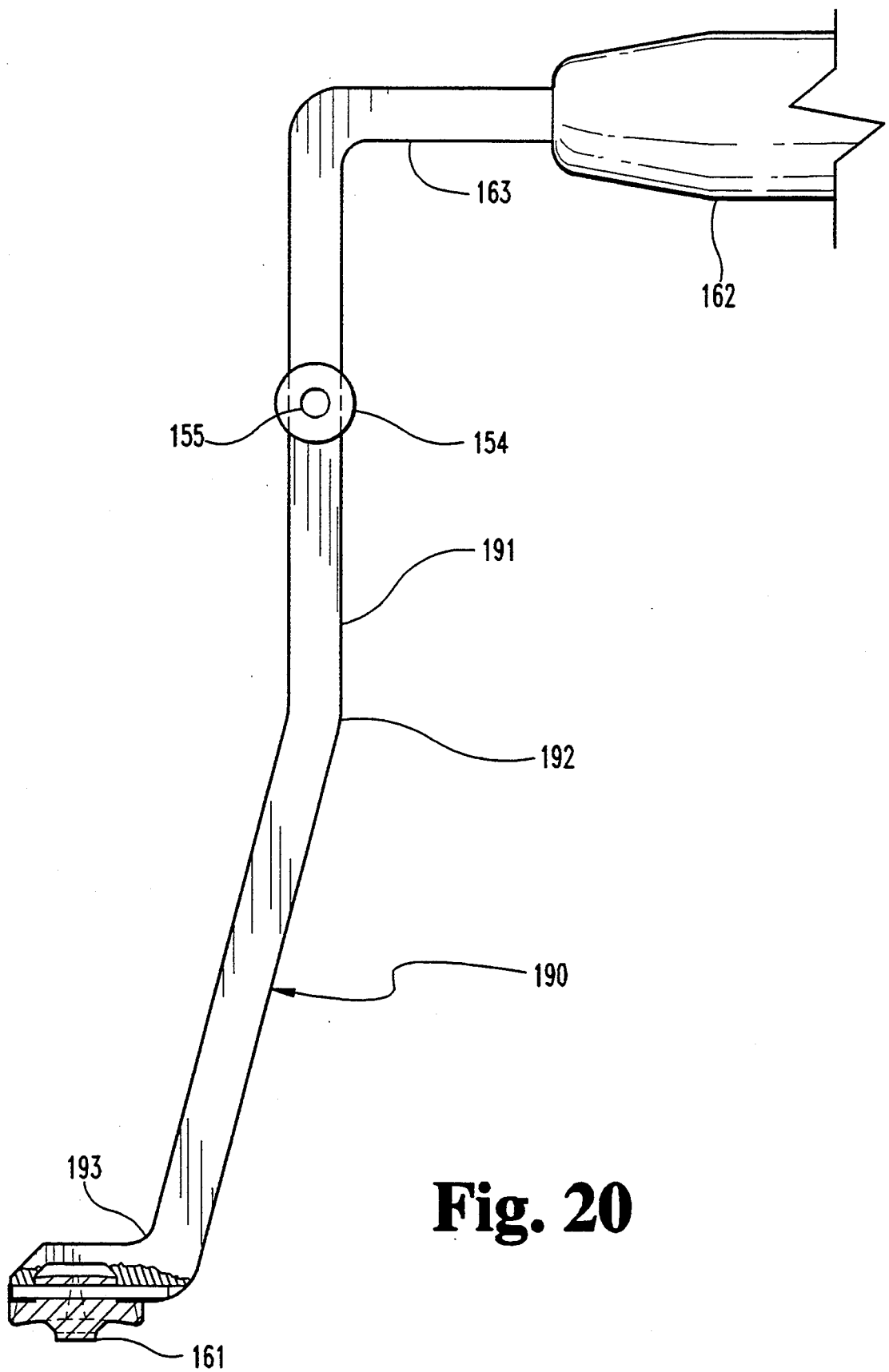
FIG. 20 is a side cross-sectional view of the invention.

In an alternative embodiment 190 shown in FIG. 20, the configuration of the guide 190 increases the surgical view of the implant. The bridge portion 163 is attached to the arm 191 at a 90° angle. The arm 191 is slightly bent at a point 192 and is provided with a wrist 193. In this configuration, the guide 190 does not obstruct the view of the surgical worksite.

While the invention has been illustrated and described in detail in the drawings and foregoing description, the stone is to be considered as illustrative and not restrictive in character, it being understood that only the preferred embodiments have been shown and described and that all changes and modifications that come within the spirit of the invention are desired to be protected.

What is claimed is:

1. A holder drill guide tool for accurately drilling fixation holes into vertebrae to be instrumented with a spinal plate having screw bores, comprising:
    a first arm and a second arm, said first arm attached to said second arm, each said arm having a proximal end and a distal end;
    a first foot attached to the proximal end of said first are and a second foot attached to the proximal end of said second arm, each said foot defining a number of thru-holes sized to receive a drilling tool, each said hole being disposed in alignment with a screw bore in the spinal plate when the tool is engaged to a spinal plate;
    a hook attached to each said foot, said hook defining a surface for engaging an edge of the spinal plate; and
    a locking mechanism configured to lock said feet in a position relative to each other to engage the spinal plate between said hook of each said foot with said thru-holes aligned with the plate screw bores.

2. The holder drill guide tool of claim 1, wherein:
    said arms are pivotally attached at a pivot; and
    the locking mechanism includes a threaded rod threadedly engaged between said first and second arms apart from said pivot,
    whereby said arms rotate about said pivot as said threaded rod is rotated, to thereby vary the relative position of said feet.

3. The holder drill guide tool of claim 2, wherein the second arm is shorter than the first arm and is pivotally attached to the first arm at a pivot point by a pivot bolt.

4. The holder drill guide tool of claim 1, wherein said feet are pivotally attached to said arms.

5. A system for accurately drilling fixation holes into vertebrae to be instrumented with a spinal plate, comprising:

a spinal plate having a lower surface adapted to engage a vertebra and an opposite upper surface and including;

a number of screw bores defined through said plate between said lower and upper surfaces and adapted to receive spinal screws therethrough; and a fixation bore defined through said plate adjacent said number of bores;

a drill guide including;

a guide body having a lower surface configured for juxtaposition with said upper surface of said spinal plate and defining a guide bore and a positioning screw bore therethrough, wherein said guide bore is arranged to align with one of said number of screw bores and said positioning screw bore is arranged to align with said fixation bore when said guide body is juxtaposed with said spinal plate;

a positioning screw adapted to be received between said spinal plate and said guide body within said fixation bore and said positioning screw bore;

said positioning screw bore having means for rigidly engaging one end of said positioning screw to said guide body; and said fixation bore having means for rigidly engaging an opposite end of said positioning screw to said spinal plate.

6. The system of claim 5 further comprising an elongated sleeve having a first end configured to be received within said guide bore of said guide body, said sleeve having a drill bore therethrough.

7. The system of claim 6, further comprising an elongated drill having a shank configured to be rotatably received within said drill bore in said elongated sleeve, and further having a drill tip for drilling into bone.

8. A system for accurately drilling fixation holes into vertebrae to be instrumented with a spinal plate, comprising:

a spinal plate having a lower surface adapted to engage a vertebra and an opposite upper surface, the plate including:

a first end and a second end; and a number of screw bores defined through said plate between said lower and upper surfaces and adapted to receive spinal screws therethrough;

a holder-drill guide, including;

a first arm and a second arm, said first arm attached to said second arm, each said arm having a proximal end and a distal end;

a first foot attached to the proximal end of said first arm and a second foot attached to the proximal end of said second arm, each said foot defining a number of thru-holes sized to receive a drilling tool, each said hole being disposed in alignment with a screw bore in the spinal plate when the tool is engaged to a spinal plate;

a hook attached to each said foot, said hook defining a surface for engaging an edge of the spinal plate; and a locking mechanism configured to lock said feet in a position relative to each other to engage the spinal plate between said hook of each said foot with said thru-holes aligned with the plate screw bores.

9. The system of claim 8, further comprising:

a number of double-headed fixation pins, each said pin having:

a first head having a diameter greater than the diameter of the thru-holes in the feet;

a second head having a diameter greater than the screw bores in the plate but smaller them the diameter of the thru-holes in the feet;

a neck portion connecting the first and second heads; and a shaft portion having a first end attached to the second head, said shaft portion sized for insertion through the thru-holes in the feet, and a second end tapering to a point for insertion into the vertebra.

10. The system of claim 8 wherein each end of the plate defines a notch on the lower surface of the plate for receiving the hook on each foot.

11. The system of claim 8 wherein said plate has a pair of screw bores defined at both of said first and second ends between said lower and upper surfaces and displaced from each other transverse to said longitudinal axis of the plate, said pair of screw bores having centerlines that diverge relative to each other below said lower surface of said plate; and said thru-holes in said feet diverge relative to each other to align with said centerlines of said screw bores.

12. The system of claim 11 wherein:

each of said screw bores includes a spherical recess defined in said plate from said top surface; and said second head of the double headed pin is sized and shaped to be received within said recess.

13. A holder drill guide tool for accurately drilling fixation holes into vertebrae to be instrumented with a spinal plate having screw bores, the tool comprising:

a pair of feet each having:

a number of thru-holes, each said hole disposed in alignment with a screw bore in a spinal plate when the tool is engaged to the spinal plate;

a hook attached to each said foot, each said hook defining a surface for engaging an edge of the spinal plate; and a locking mechanism configured to lock said feet in a position relative to each other to engage the spinal plate between said hook of each said foot with said thru-holes aligned with the plate screw bores.

14. A method for accurately drilling fixation holes into vertebrae and instrumenting the vertebrae with a spinal plate, comprising:

mounting a spinal plate against a surface of a vertebral body, said plate having a number of screw bores therethrough;

attaching a holder-drill guide tool to said spinal plate, the tool having a number of thru-holes therethrough, each of said thru-holes aligned with one of said plate screw bores;

placing a drill-tap sleeve in one of said thru-holes in said tool;

drilling the vertebra through said sleeve and screw bore;

removing said sleeve and guide from said plate; and seating a bone screw through said screw bore in said plate.

15. The method of claim 14, wherein said tool includes:

a number of feet having a number of thru-holes; and a locking mechanism configured to lock said feet to said spinal plate and further wherein the step of attaching the holder-drill guide tool to the spinal plate includes engaging the feet to the spinal plate with the thru-holes aligned with the screw bores in the plate and locking the feet together about the plate.

16. The method of claim 15, wherein the step of attaching the holder-drill guide tool to the spinal plate further includes mounting said spinal plate against the surface of the vertebral body with a hook attached to an edge of each said foot.

17. The method of claim 14, wherein the step of attaching the holder-drill guide tool to the spinal plate includes extending a number of double headed fixation pins through the aligned thru-holes and screw bores and into the vertebra, the fixation pins having;
- a first head having a diameter greater than the diameter of said thru-holes in said feet;
- a second head having a diameter greater than said screw bores in said spinal plate but smaller than the diameter of said thru-holes in said feet;
- a neck portion connecting said first and second heads; and
- a shaft portion having a first end attached to said second head and a second end tapering to a point.

* * * * *

UNITED STATES PATENT AND TRADEMARK OFFICE
CERTIFICATE OF CORRECTION

PATENT NO. : 5,423,826
DATED : June 13, 1995
INVENTOR(S) : Bradley J. Coates and Gary L. Lowery It is certified that error appears in the above-identified patent and that said Letters Patent is hereby corrected as shown below:

Column 2, line 13; please change "stone" to "same";

Column 2, line 52; please delete "and";

Column 6, line 62, please change "725" to "7.25";

Column 8, line 1, please change "the plate" to "in the plate";

Column 8, line 4, please change "to" to "into";

Column 8, line 16, please change "memos" to "means";

Column 11, line 30, please delete "to";

Column 14, line 42, please change "are" to "arm";

Column 16, line 7, please change "them" to "than".

Signed and Sealed this

Nineteenth Day of March, 1996

Attest:

BRUCE LEHMAN

Attesting Officer     Commissioner of Patents and Trademarks